United States Patent [19]
McCleary

[11] 4,321,364
[45] Mar. 23, 1982

[54] PREPARATION OF SOLUBLE CHROMOGENIC SUBSTRATES

[75] Inventor: Barry V. McCleary, South Penrith, Australia

[73] Assignee: Minister for Public Works for the State of New South Wales, Sydney, Australia

[21] Appl. No.: 141,149

[22] Filed: Apr. 17, 1980

[51] Int. Cl.³ .............................................. C08B 37/00
[52] U.S. Cl. ..................................... 536/18; 435/18; 435/22; 536/45; 536/56; 536/117; 536/118; 536/120
[58] Field of Search ............... 435/18, 22, 96; 536/45, 536/56, 102, 18, 117, 118, 120

[56] References Cited

U.S. PATENT DOCUMENTS

| | | | |
|---|---|---|---|
| 3,413,198 | 11/1968 | Deutsch | 435/4 |
| 3,597,322 | 8/1971 | Babson | 435/22 |
| 3,616,251 | 10/1971 | Linoli | 23/230 B |
| 3,676,303 | 7/1972 | Bjorn et al. | 435/18 |
| 3,676,303 | 7/1972 | Ingelman | 435/22 |
| 3,679,661 | 7/1972 | Babson | 435/22 |
| 3,758,384 | 9/1973 | Babson et al. | 435/22 |
| 3,773,626 | 11/1973 | Bernt et al. | 435/19 |
| 3,788,946 | 1/1974 | Kurimoto et al. | 435/22 |
| 3,817,838 | 6/1974 | Harris et al. | 435/19 |
| 3,852,157 | 12/1974 | Rubenstein et al. | 424/12 |
| 3,869,348 | 3/1975 | Gindler | 435/22 |
| 3,878,048 | 4/1975 | Carroll | 252/408 R |
| 3,884,764 | 5/1975 | Goodhue et al. | 435/11 |
| 3,892,631 | 7/1975 | Carroll | 435/24 |
| 3,905,871 | 9/1975 | Rubenstein et al. | 435/188 |
| 3,953,297 | 4/1976 | Gindler | 435/22 |
| 4,000,118 | 12/1976 | Dawson et al. | 536/56 |
| 4,022,667 | 5/1977 | Myrick et al. | 435/19 |
| 4,025,392 | 5/1977 | Dougherty | 435/22 |
| 4,066,509 | 1/1978 | Ceska | 435/22 |
| 4,137,225 | 1/1979 | Afekenstam | 260/112.5 R |
| 4,144,306 | 3/1979 | Figueras | 435/14 |
| 4,155,884 | 5/1979 | Hughes | 536/102 |
| 4,168,203 | 9/1979 | Takahashi et al. | 435/21 |

OTHER PUBLICATIONS

Kline et al., "A Rapid Assay of Serum Amylase", Clin. Chem., vol. 16, No. 1, 1970, p. 32.
Huang et al., "Sensitive Assay for Cellulose and Dextranase", Anal. Biochem., 1976, pp. 369–377.
Thewlis, Die Starke, vol. 21, 1969, p. 21.
Brochure Describing Dyamyl-1, (General Diagnostics).
Brochure Describing Amylchrome.
Babson et al., "New Amylase Substrate & Assay Procedure", Clin. Chem., vol. 16, No. 1, 1970, p. 39.
Sax et al., "Determination of Serum and Urine Amylase", Clin. Chem., vol. 17, No. 4, 1971, p. 311.

Primary Examiner—Peter A. Hruskoci
Attorney, Agent, or Firm—Laubscher, Philpitt & Laubscher

[57] ABSTRACT

A chromogenic substrate for the assay of polysaccharide endo-hydrolases is the reaction product of a polysaccharide susceptible to endo-hydrolase degradation, a chemical reagent for increasing the solubility of the polysaccharide so as to increase its susceptibility to enzyme degradation, and a dye substance for coloring the polysaccharide and rendering it capable of estimation by absorption spectrometry. The amount of chemical reagent should be such as to produce a degree of chemical substitution in the range 0.06 to 0.6 DS.

7 Claims, No Drawings

PREPARATION OF SOLUBLE CHROMOGENIC SUBSTRATES

FIELD OF THE INVENTION

This invention relates to the production of chromogenic substrates, and particularly to the production of chromogenic substrates of increased solubility for the assay of polysaccharide endo-hydrolases. More especially the invention relates to the production of chromogenic substrates of increased solubility for the assay of polysaccharide endo-hydrolases by either dyeing polysaccharides which have been chemically substituted to increase solubility, or alternatively by chemically substituting dyed polysaccharides to increase solubility.

BACKGROUND OF THE INVENTION

The use of chromogenic, that is dye-labelled, substrates for the assay of polysaccharide endo-hydrolases is well known; however the substrates used hitherto suffer from serious disadvantages. Thus most substrates currently available are insoluble, for example those marketed under the trade marks "Phadebas" (Pharmacia South Seas Co.) and "Amylochrome" (Roche Diagnostics), and also dyed amylose (Calbiochem Co.) and amylopectin (Sigma Chemical Co.).

Two soluble dyed substrates are available, namely "Dyamyl-L" (Reactone Red 2B-amylopectin) from General Diagnostics and Lyosine Red (P.. Brilliant Red M-2B5-Amylopectin) from Reliable Reagents Co. Soluble substrates are advantageous because in general they are more susceptible to enzyme hydrolysis, thereby imparting a greater sensitivity to the assay procedure; also enzymes have a greater affinity for soluble substrates so that in order to obtain maximum reaction rates much lower concentrations of the substrate can be used in the assay mixture. However, the soluble substrates currently available are difficult to prepare and are correspondingly expensive; one difficulty in their preparation is the separation of the dyed polysaccharide from free dye which involves a laborious and time consuming gel filtration step using a media such as the molecular sieve "Sephadex G25".

SUMMARY OF THE INVENTION

The present invention provides improved soluble chromogenic substrates and a method for producing them in a cheap and convenient manner, the substrates providing a high sensitivity and being simple to use in assay procedures.

According to the present invention there is provided a chromogenic substrate comprising a dyed polysaccharide, the polysaccharide having been chemically treated to increase its solubility. The polysaccharide may be chemically treated prior to dyeing, or alternatively it may be dyed and chemically treated subsequently.

The idea of chemically treating polysaccharides is not in itself novel and, for example, has been described by Thewlis (1969), Die Starke, 21, 21-24. The use of treated and dyed polysaccharides as substrates for the assay of polysaccharide endo-hydrolases has not, however, previously been proposed.

A wide range of chemical treatments can be employed to increase solubility, for example, carboxymethylation as described by Thewlis, but also hydroxypropylation, hydroxyethylation, quaternisation, sulphation, phosphation, nitration, treatment with 2-chloro-N,N-diethyl ethylamine, and many other methods. The actual chemical treatment is not critical; however, it has been found that the degree of chemical substitution required to provide an effective substrate is critical and must be within the range of 0.06-0.6 DS (degrees of substitution). At degrees of substitution below 0.06 the product is quite insoluble while at values above 0.6 the substrate is resistant to enzyme attack. The optimum range will vary somewhat depending upon the chemical treatment used but generally a range 0.1-0.4 DS is preferred.

The preferred level of dyed substitution has been found to be between 1 dye molecule: 15 sugar molecules and 1 dye molecule: 150 sugar molecules. Substrates at each end of the above range possess particular advantages; thus a 1:15 ratio provides a highly sensitive but relatively less soluble substrate whereas a 1:150 ratio provides a less sensitive but much more soluble substrate.

Substrates according to the invention can be produced easily and cheaply. In particular, the dyed treated polysaccharide can be easily separated from free dye by precipitation, for example with acidic ethanol, a technique which has been found not to work in the preparation of known soluble substrates, viz Dyamyl-L and Lyosine Red. This precipitation technique for removal of free dye greatly reduces the time involved in preparing substrates according to the invention, and correspondingly reduces the cost of production.

The process of the present invention can be used to produce a wide range of substrates for assaying polysaccharide endo-hydrolases, for example for assaying α-amylase, endo-β 1-4 mannanase and endo-β 1-4 glucanase; as well, numerous other polysaccharides can be used for the preparation of substrates such as galactans, arabinans, pectic substances, dextran, α-mannans and so on. Moreover, the present invention can be used to produce substrates for the assay of some polysaccharide endo-hydrolases for which substrates are not now commercially available.

Substrates according to the invention can be used to allow the simple and inexpensive assaying of a wide range of specimens, for example α-amylase in blood-serum, urine, brewers' malt and cereal grains; also for the major enzymes involved in digesting woody materials viz: endo-β 1-4 cellulase, endo-β 1-4 xylanase and endo-β 1-4 mannanase, which will assist investigations into the digestion of woody materials and agricultural waste products in "single-cell protein" research, and also into the digestion of cellulosic and hemicellulosic materials in ruminants.

DESCRIPTION OF SPECIFIC EMBODIMENTS

Preparation of Chromogenic Carboxymethyl Polysaccharides

The invention is illustrated with reference to the following specific Examples 1 and 2.

EXAMPLE 1

To 100 g of amylose (corn, potato or other) in a 1 liter flask fitted with a reflux condenser, stirrer and tap funnel, is added a solution of 9.6 g of monochloroacetic acid in 259 ml of ethanol. This solution is stirred and brought to reflux temperature (80° C.) and a solution of 12.8 g of NaOH dissolved in 40 ml of $H_2O$ all added to 360 ml of ethanol, is run in slowly, the whole being then boiled for a further 15 min. On cooling, the product is filtered off, washed with 80% ethanol and then added to 1 liter of boiling water. On dissolution, the temperature is lowered to 60° C. and 20 g Remazolbrilliant Blue R and 100 g sodium sulphate added with stirring. Stirring is maintained for 30 min. with addition of 10 g trisodium phosphate dissolved in 20 ml of water. Stirring is continued for a further 30 min. The solution is then poured, with stirring, into 2 l of acidic ethanol (5% conc. HCl in ethanol). The rubbery precipitate is collected, squeezed free of excess liquid and redissolved in 1 l of hot water. The precipitation step is repeated a further two times by which stage essentially all the free dye is removed. The material is redissolved and then 2 l of ethanol are added gradually. The resultant precipitate is washed with ethanol and acetone and dried. The resultant product has a carboxymethylation degree of substitution of approx. 0.1 and a Remazolbrilliant Blue R to anhydrohexose ratio of approximately 1:50.

Carboxymethylation of starch, amylopectin, xylan (wheat straw or larch wood) and mannan (palm seeds) is also performed as described above. The products obtained when similar levels of chloroacetic acid are used, have similar degrees of carboxymethyl substitution.

These polysaccharides were dyed as for amylose, with 20 g dye per 100 g of polysaccharide. However, many other dyes, especially Remazolbrilliant Black B can also be employed. All substrates with a DS of 0.1 to 0.2 and a dye carbohydrate ratio of 1:50, are soluble/gelatinous suspensions and are highly susceptible to the respective endo-polysaccharase but completely resistant to exo-polysaccharases, e.g. $\beta$-amylase and amyloglucosidase in the case of dyed carboxymethyl amylose, amylopectin and starch.

EXAMPLE 2

Commercially available carboxymethyl cellulose with a degree of substitution of approximately 0.2 to 0.5 (e.g. Hercules Co. carboxymethyl cellulose 4M6SF, DS=0.35-0.45) (50 g) is added with stirring to a solution of 50 mg of cellulase (Sigma Chemical Co.—Cat No. C7502) in one liter of 0.1 M KCl (40° C.) over a period of 30 min. The solution is then blended vigorously and incubated a further 30 min. at 40° C. to allow partial depolymerization of the carboxymethyl cellulose.

Remazolbrilliant Blue R (10 g) or Remazolbrilliant Black B (10 g) and sodium sulphate (100 g) are then added to the solution and dissolved with stirring. The temperature is increased to 60° C. and the solution stirred for a further 30 min. Trisodium phosphate (10 g) is then added and stirring continued for a further 30 min. The solution is poured into acidic ethanol and the dyed polysaccharide recovered as described in Example 1.

Dissolution of Substrates

Dissolution of substrates according to the invention is illustrated with reference to the following Examples 3 and 4.

EXAMPLE 3—Remazolbrilliant Blue R—Carboxymethyl Amylose

Substrate (2 g) was sprinkled into a beaker of vigorously stirred hot water with the addition of a few drops of sodium hydroxide solution (10% w/v) to neutralise traces of acid remaining in the polysaccharide from the preparation step. On stirring at 80°-90° C. for about 5 min., an aliquot (5 ml) of the desired buffer (2 M) was added and stirring continued. On complete dissolution the solution was cooled and the volume adjusted to 100 ml. The final preparation contained dyed substrate (2%) in 0.1 M buffer (phosphate or acetate) of desired pH.

EXAMPLE 4—Remazolbrilliant Blue R—Carboxymethyl cellulose

Substrate (1 g) was sprinkled into a stirred beaker containing 1% NaOH (20 ml). Stirring was continued for 2 min. and water (40 ml) added with further stirring for a few min. followed by blending with an Ultra Turrax for 30 sec. HCl (2 ml), 2.5 M) was added to neutralise the solution and then acetate buffer (15 ml, 2 M, pH5) was added. The volume was then adjusted to 100 ml.

Assay of Polysaccharide Endohydrolases

The assay of polysaccharide endohydrolases using substrates according to the invention is illustrated in the following Examples 5 and 6.

EXAMPLE 5—Assay of $\alpha$-Amylase

The assay procedure involved incubating 0.1 ml. of enzyme preparation with 0.5 ml of substrate (2%) at 37° or 40° C. Reaction was terminated by adding 2.5 ml of a precipitant containing 80% ethyleneglycol mono methyl ether; 0.3 M sodium acetate buffer, pH5; and 0.4% zinc acetate. The solution was stirred, centrifuged (1,000 g) and the absorbance (590 nm) of the supernatant solution measured. This absorbance value can be directly related to International Enzyme Units of activity.

EXAMPLE 6—Assay of $\beta$-Glucanase, $\beta$-Mannanase and $\beta$-Xylanase

Enzyme preparation (0.5 ml) is incubated with substrate (0.1 ml, 1.0%) at 40° C. Reaction is terminated and unhydrolysed dyed polysaccharide precipitated by the addition of an aliquot (3 ml) of acidic ethanol (5% HCl in ethanol).

I claim:

1. A chromogenic substrate capable of being hydrolyzed by polysaccharide endo-hydrolases for the assay thereof, which is a reaction product of
   (a) a polysaccharide susceptible to endo-hydrolase degradation;
   (b) a chemical reagent capable of reacting with said polysaccharide to produce a product whose solubility is increased with respect to the solubility of said polysaccharide without substantially reducing the susceptibility to endo-hydrolase degradation; and
   (c) a dye substance capable of reacting with said polysaccharide to produce a water soluble dyed coloured product; the reaction of the polysaccharide with said chemical having been carried out with an amount of said chemical reagent such as to produce a degree of chemical substitution of the polysaccharide in the range 0.06 to 0.6 degrees of substitution.

2. A chromogenic substrate according to claim 1, wherein said degree of chemical substitution is in the range 0.1 to 0.4 DS.

3. A chromogenic substrate according to claim 1, wherein said chemical reagent is capable of effecting on the polysaccharide a chemical reaction selected from carboxymethylation, hydroxypropylation, hydroxyethylation, quaternisation, sulphation, phosphation, and nitration.

4. A chromogenic substrate according to claim 1, wherein said chemical reagent is 2-chloro-N,N-diethyl ethylamine.

5. A chromogenic substrate according to claim 1, wherein said dye substance is reacted with an amount of polysaccharide in the range of 1 dye molecule:15 to 150 sugar moieties.

6. A chromogenic substrate according to claim 1, wherein the polysaccharide is reacted with said chemical reagent prior to reaction of the chemically treated polysaccharide produced with said dye substance.

7. A method for preparing a chromogenic substrate capable of being hydrolyzed by endo-hydrolases for the assay thereof, which comprises reacting (a) A polysaccharide susceptible to endo-hydrolase degradation;

(b) a chemical reagent capable of reacting with said polysaccharide to produce a product whose solubility is increased with respect to the solubility of said polysaccharide without substantially reducing the susceptibility to endo-hydrolase degradation; and (c) a dye substance capable of reacting with said polysaccharide to produce a water soluble dyed colored product;

the reaction of said polysaccharide with said chemical reagent having been carried out with an amount of said chemical reagent such as to produce a degree of chemical substitution of the polysaccharide in the range of 0.06 to 0.6 degrees of substitution.

* * * * *